US010695178B2

(12) United States Patent
Zentgraf et al.

(10) Patent No.: US 10,695,178 B2
(45) Date of Patent: Jun. 30, 2020

(54) MINIMALLY INVASIVE REPAIR OF HEART VALVE LEAFLETS

(71) Applicant: NeoChord, Inc., St. Louis Park, MN (US)

(72) Inventors: John Zentgraf, Minneapolis, MN (US); David J. Parins, Corcoran, MN (US); Arun Saini, Burnsville, MN (US)

(73) Assignee: NeoChord, Inc., St. Louis Park, MN (US)

(*) Notice: Subject to any disclaimer, the term of this patent is extended or adjusted under 35 U.S.C. 154(b) by 1011 days.

(21) Appl. No.: 14/947,399

(22) Filed: Nov. 20, 2015

(65) Prior Publication Data
US 2016/0143737 A1 May 26, 2016

Related U.S. Application Data

(63) Continuation of application No. 13/486,632, filed on Jun. 1, 2012, now abandoned.
(Continued)

(51) Int. Cl.
A61F 2/24 (2006.01)
A61B 17/00 (2006.01)
(Continued)

(52) U.S. Cl.
CPC ........ A61F 2/2457 (2013.01); A61B 17/0057 (2013.01); A61B 17/0467 (2013.01);
(Continued)

(58) Field of Classification Search
CPC ........... A61F 2/2457; A61F 2250/0012; A61B 17/0467; A61B 17/0482; A61B 17/0487;
(Continued)

(56) References Cited

U.S. PATENT DOCUMENTS 2,751,908 A 6/1956 Wallace
3,667,474 A 6/1972 Lapkin
(Continued)

FOREIGN PATENT DOCUMENTS

EP 1039851 B1 7/2005
EP 1637091 A2 3/2006
(Continued)

OTHER PUBLICATIONS

Interactive Cardio Vascular and Thoracic Surgery; Abstracts; Suppl 3 to vol. 7 (Sep. 2008) 52 pages.
(Continued)

Primary Examiner — Tan-Uyen T Ho
Assistant Examiner — Rachel S Highland
(74) Attorney, Agent, or Firm — Patterson Thuente Pedersen, P.A.

(57) ABSTRACT

A method of repairing a heart valve provides intravascular access for repair of a heart valve through a ventricular trans-septal approach. An external guide catheter can be inserted through a vein of a patient into the right ventricle via the right atrium. An internal guide catheter can be inserted through the external guide and can provide access to the septum for a puncture tool to create an opening through the septum to the left ventricle. The internal guide can then be advanced into the left ventricle and used to guide a deployment catheter that deploys a repair device onto the heart valve.

17 Claims, 12 Drawing Sheets

Related U.S. Application Data

(60) Provisional application No. 61/492,135, filed on Jun. 1, 2011.

(51) Int. Cl.
*A61B 17/04* (2006.01)
*A61B 17/06* (2006.01)

(52) U.S. Cl.
CPC ...... *A61B 17/0469* (2013.01); *A61B 17/0482* (2013.01); *A61B 17/0487* (2013.01); *A61B 2017/00243* (2013.01); *A61B 2017/00606* (2013.01); *A61B 2017/0456* (2013.01); *A61B 2017/0496* (2013.01); *A61B 2017/06042* (2013.01); *A61F 2250/0012* (2013.01)

(58) Field of Classification Search
CPC ............ A61B 17/0057; A61B 17/0469; A61B 2017/00243; A61B 2017/0496; A61B 2017/00606; A61B 2017/0456; A61B 2017/06042
See application file for complete search history.

(56) References Cited

U.S. PATENT DOCUMENTS

| | | |
|---|---|---|
| 3,842,840 A | 10/1974 | Schweizer |
| 4,258,716 A | 3/1981 | Sutherland |
| 4,351,345 A | 9/1982 | Carney |
| 4,836,204 A | 6/1989 | Landymore et al. |
| 4,935,027 A | 6/1990 | Yoon |
| 4,957,498 A | 9/1990 | Caspari et al. |
| 4,967,498 A | 9/1990 | Caspari |
| 4,960,424 A | 10/1990 | Grooters |
| 4,967,798 A | 11/1990 | Hammer |
| 4,972,874 A | 11/1990 | Jackson |
| 5,053,013 A | 10/1991 | Ensminger |
| 5,059,201 A | 10/1991 | Asnis |
| 5,211,650 A | 5/1993 | Noda |
| 5,297,536 A | 3/1994 | Wilk |
| 5,304,185 A | 4/1994 | Taylor |
| 5,312,423 A | 5/1994 | Rosenbluth et al. |
| 5,336,229 A | 8/1994 | Noda |
| 5,383,877 A | 1/1995 | Clarke |
| 5,431,666 A | 7/1995 | Sauer et al. |
| 5,452,733 A | 9/1995 | Sterman |
| 5,474,519 A | 12/1995 | Bloomer |
| 5,547,455 A | 8/1996 | McKenna et al. |
| 5,556,411 A | 9/1996 | Taoda et al. |
| 5,571,215 A | 11/1996 | Sterman |
| 5,601,578 A | 2/1997 | Murphy |
| 5,626,607 A | 5/1997 | Malecki |
| 5,653,716 A | 8/1997 | Malo et al. |
| 5,665,100 A | 9/1997 | Yoon |
| 5,667,472 A | 9/1997 | Finn et al. |
| 5,667,473 A | 9/1997 | Finn et al. |
| 5,667,478 A | 9/1997 | McFarlin et al. |
| 5,693,091 A | 12/1997 | Larson, Jr. et al. |
| 5,728,113 A | 3/1998 | Sherts |
| 5,762,458 A | 6/1998 | Wang et al. |
| 5,762,613 A | 6/1998 | Sutton et al. |
| 5,766,163 A | 6/1998 | Mueller et al. |
| 5,772,597 A | 6/1998 | Goldberger et al. |
| 5,772,672 A | 6/1998 | Toy et al. |
| 5,785,658 A | 7/1998 | Benaron et al. |
| 5,797,960 A | 8/1998 | Stevens et al. |
| 5,830,231 A | 11/1998 | Geiges, Jr. |
| 5,839,639 A | 11/1998 | Sauer et al. |
| 5,897,564 A | 4/1999 | Schulze et al. |
| 5,908,428 A | 6/1999 | Scirica et al. |
| 5,908,429 A | 6/1999 | Yoon |
| 5,919,128 A | 7/1999 | Fitch |
| 5,961,440 A | 10/1999 | Schweich, Jr. |
| 5,972,004 A | 10/1999 | Williamson et al. |
| 5,972,030 A | 10/1999 | Garrison et al. |
| 5,984,939 A | 11/1999 | Yoon |
| 5,993,466 A | 11/1999 | Yoon |
| 5,993,467 A | 11/1999 | Yoon |
| 6,022,360 A | 2/2000 | Reimels et al. |
| 6,045,497 A | 4/2000 | Schweich, Jr. |
| 6,050,936 A | 4/2000 | Schweich, Jr. |
| 6,053,933 A | 4/2000 | Balazs et al. |
| 6,059,715 A | 5/2000 | Schweich, Jr. |
| 6,077,214 A | 6/2000 | Mortier et al. |
| 6,117,144 A | 9/2000 | Nobles et al. |
| 6,129,683 A | 10/2000 | Sutton et al. |
| 6,149,660 A | 11/2000 | Laufer et al. |
| 6,152,934 A | 11/2000 | Harper et al. |
| 6,162,168 A | 12/2000 | Schweich, Jr. |
| 6,162,233 A | 12/2000 | Williamson |
| 6,165,119 A | 12/2000 | Schweich, Jr. |
| 6,165,120 A | 12/2000 | Schweich, Jr. |
| 6,165,183 A | 12/2000 | Kuehn et al. |
| 6,178,346 B1 | 1/2001 | Amundson et al. |
| 6,183,411 B1 | 2/2001 | Mortier et al. |
| 6,190,357 B1 | 2/2001 | Ferrari et al. |
| 6,234,079 B1 | 5/2001 | Chertkow |
| 6,234,995 B1 | 5/2001 | Peacock, III |
| 6,245,079 B1 | 6/2001 | Nobles et al. |
| 6,260,552 B1 | 7/2001 | Mortier et al. |
| 6,261,222 B1 | 7/2001 | Schweich, Jr. |
| 6,264,602 B1 | 7/2001 | Mortier et al. |
| 6,269,819 B1 | 8/2001 | Oz et al. |
| 6,270,508 B1 | 8/2001 | Klleman et al. |
| 6,283,993 B1 | 9/2001 | Cosgrove et al. |
| 6,312,447 B1 | 11/2001 | Grimes |
| 6,332,863 B1 | 12/2001 | Schweich, Jr. et al. |
| 6,332,864 B1 | 12/2001 | Schweich, Jr. et al. |
| 6,332,893 B1 | 12/2001 | Mortier et al. |
| 6,355,050 B1 | 3/2002 | Andreas et al. |
| 6,401,720 B1 | 6/2002 | Stevens et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,419,626 B1 | 7/2002 | Yoon |
| 6,436,107 B1 | 8/2002 | Wang et al. |
| 6,443,922 B1 | 9/2002 | Roberts et al. |
| 6,451,054 B1 | 9/2002 | Stevens |
| 6,461,366 B1 | 10/2002 | Seguin |
| 6,508,777 B1 | 1/2003 | Macoviak et al. |
| 6,514,194 B2 | 2/2003 | Schweich, Jr. et al. |
| 6,533,796 B1 | 3/2003 | Sauer et al. |
| 6,537,198 B1 | 3/2003 | Vidlund et al. |
| 6,537,314 B2 | 3/2003 | Langberg et al. |
| 6,551,331 B2 | 4/2003 | Nobles et al. |
| 6,558,416 B2 | 5/2003 | Cosgrove et al. |
| 6,562,052 B2 | 5/2003 | Nobles et al. |
| 6,564,805 B2 | 5/2003 | Garrison et al. |
| 6,582,388 B1 | 6/2003 | Coleman et al. |
| 6,585,727 B1 | 7/2003 | Cashman et al. |
| 6,589,160 B2 | 7/2003 | Schweich, Jr. et al. |
| 6,602,288 B1 | 8/2003 | Cosgrove et al. |
| 6,616,684 B1 | 9/2003 | Vidlund et al. |
| 6,619,291 B2 | 9/2003 | Hlavka et al. |
| 6,622,730 B2 | 9/2003 | Ekvall et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,629,984 B1 | 10/2003 | Chan |
| 6,645,205 B2 | 11/2003 | Ginn |
| 6,679,268 B2 | 1/2004 | Stevens et al. |
| 6,692,605 B2 | 2/2004 | Kerr et al. |
| 6,695,866 B1 | 2/2004 | Kuehn et al. |
| 6,709,456 B2 | 3/2004 | Langberg et al. |
| 6,718,985 B2 | 4/2004 | Hlavka et al. |
| 6,723,038 B1 | 4/2004 | Schroeder et al. |
| 6,733,509 B2 | 5/2004 | Nobles et al. |
| 6,740,107 B2 | 5/2004 | Loeb et al. |
| 6,743,239 B1* | 6/2004 | Kuehn ............... A61B 17/0643 464/149 |
| 6,746,471 B2 | 6/2004 | Mortier et al. |
| 6,752,713 B2 | 6/2004 | Johnson, Jr. |

(56) References Cited

U.S. PATENT DOCUMENTS

| | | | |
|---|---|---|---|
| 6,752,813 B2 | 6/2004 | Goldfarb et al. |
| 6,755,777 B2 | 6/2004 | Schweich, Jr. et al. |
| 6,764,510 B2 | 7/2004 | Vidlund et al. |
| 6,770,083 B2 | 8/2004 | Seguin |
| 6,770,084 B1 | 8/2004 | Bain et al. |
| 6,793,618 B2 | 9/2004 | Schweich, Jr. et al. |
| 6,802,860 B2 | 10/2004 | Cosgrove et al. |
| 6,808,488 B2 | 10/2004 | Mortier et al. |
| 6,810,882 B2 | 11/2004 | Langberg et al. |
| 6,840,246 B2 | 1/2005 | Downing |
| 6,858,003 B2 | 2/2005 | Evans et al. |
| 6,875,224 B2 | 4/2005 | Grimes |
| 6,893,448 B2 | 5/2005 | O'Quinn et al. |
| 6,908,424 B2 | 6/2005 | Mortier et al. |
| 6,918,917 B1 | 7/2005 | Nguyen et al. |
| 6,921,407 B2 | 7/2005 | Nguyen et al. |
| 6,929,715 B2 | 8/2005 | Fladda et al. |
| 6,936,054 B2 | 8/2005 | Chu |
| 6,955,175 B2 | 10/2005 | Stevens et al. |
| 6,962,605 B2 | 11/2005 | Cosgrove et al. |
| 6,978,176 B2 | 12/2005 | Lattouf |
| 6,986,775 B2 | 1/2006 | Morales et al. |
| 6,989,028 B2 | 1/2006 | Lashinski et al. |
| 6,991,635 B2 | 1/2006 | Takamoto et al. |
| 6,997,950 B2 | 2/2006 | Chawla |
| 7,004,176 B2 | 2/2006 | Lau |
| 7,004,952 B2 | 2/2006 | Nobles et al. |
| 7,011,669 B2 | 3/2006 | Kimblad |
| 7,044,905 B2 | 5/2006 | Vidlund et al. |
| 7,048,754 B2 | 5/2006 | Martin et al. |
| 7,077,862 B2 | 7/2006 | Vidlund et al. |
| 7,083,628 B2 | 8/2006 | Bachman |
| 7,083,638 B2 | 8/2006 | Foerster |
| 7,090,686 B2 | 8/2006 | Nobles et al. |
| 7,094,244 B2 | 8/2006 | Schreck |
| 7,100,614 B2 | 9/2006 | Stevens et al. |
| 7,112,207 B2 | 9/2006 | Allen et al. |
| 7,112,219 B2 | 9/2006 | Vidlund et al. |
| 7,115,110 B2 | 10/2006 | Frazier et al. |
| 7,118,583 B2 | 10/2006 | O'Quinn et al. |
| 7,122,040 B2 | 10/2006 | Hill et al. |
| 7,179,291 B2 | 2/2007 | Rourke et al. |
| 7,186,264 B2 | 3/2007 | Liddicoat et al. |
| 7,189,199 B2 | 3/2007 | McCarthy et al. |
| 7,217,240 B2 | 5/2007 | Snow |
| 7,226,467 B2 | 6/2007 | Lucatero et al. |
| 7,247,134 B2 | 7/2007 | Vidlund et al. |
| 7,250,028 B2 | 7/2007 | Julian et al. |
| 7,288,097 B2 | 10/2007 | Seguin |
| 7,294,148 B2 | 11/2007 | McCarthy |
| 7,381,210 B2 | 6/2008 | Zarbatany et al. |
| 7,464,712 B2 | 12/2008 | Oz et al. |
| 7,563,267 B2 | 7/2009 | Goldfarb et al. |
| 7,563,273 B2 | 7/2009 | Goldfarb et al. |
| 7,604,646 B2 | 10/2009 | Goldfarb et al. |
| 7,608,091 B2 | 10/2009 | Goldfarb et al. |
| 7,635,386 B1 | 12/2009 | Gammie |
| 7,666,204 B2 | 2/2010 | Thornton et al. |
| 7,815,654 B2 | 10/2010 | Chu |
| 7,879,048 B2 | 2/2011 | Bain et al. |
| 7,887,552 B2 | 2/2011 | Bachman |
| 8,465,500 B2 | 6/2013 | Speziali |
| 8,758,393 B2 | 6/2014 | Zentgraf |
| 2001/0005787 A1 | 6/2001 | Oz |
| 2001/0016675 A1 | 8/2001 | Mortier et al. |
| 2001/0021872 A1 | 9/2001 | Bailey et al. |
| 2002/0013571 A1 | 1/2002 | Goldfarb et al. |
| 2002/0029080 A1 | 3/2002 | Mortier et al. |
| 2002/0049402 A1 | 4/2002 | Peacock, III |
| 2002/0077524 A1 | 6/2002 | Schweich, Jr. |
| 2002/0169359 A1 | 11/2002 | McCarthy |
| 2002/0173694 A1 | 11/2002 | Mortier et al. |
| 2002/0183766 A1 | 12/2002 | Seguin |
| 2002/0183787 A1* | 12/2002 | Wahr ............ A61B 17/0057 606/213 |
| 2003/0004562 A1 | 1/2003 | DiCarlo |
| 2003/0032979 A1 | 2/2003 | Mortier et al. |
| 2003/0050529 A1 | 3/2003 | Vidlund et al. |
| 2003/0050693 A1 | 3/2003 | Quijano |
| 2003/0078600 A1 | 4/2003 | O'Quinn et al. |
| 2003/0105519 A1 | 6/2003 | Fasol |
| 2003/0130731 A1 | 7/2003 | Vidlund et al. |
| 2003/0166992 A1 | 9/2003 | Schweich, Jr. |
| 2003/0167071 A1 | 9/2003 | Martin et al. |
| 2003/0171641 A1 | 9/2003 | Schweich, Jr. |
| 2003/0181928 A1 | 9/2003 | Vidlund et al. |
| 2003/0187457 A1 | 10/2003 | Weber |
| 2003/0195529 A1 | 10/2003 | Takamoto et al. |
| 2003/0199975 A1 | 10/2003 | Gabbay |
| 2004/0003819 A1 | 1/2004 | St. Goar |
| 2004/0030382 A1 | 2/2004 | St. Goar |
| 2004/0039442 A1 | 2/2004 | St. Goar |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0049552 A1 | 3/2004 | Motoyama |
| 2004/0087975 A1 | 5/2004 | Lucatero et al. |
| 2004/0087978 A1 | 5/2004 | Velez et al. |
| 2004/0092962 A1 | 5/2004 | Thornton et al. |
| 2004/0097805 A1 | 5/2004 | Verard et al. |
| 2004/0116767 A1 | 6/2004 | Lebovic |
| 2004/0122448 A1 | 6/2004 | Levine |
| 2004/0127983 A1 | 7/2004 | Mortier et al. |
| 2004/0133063 A1 | 7/2004 | McCarthy et al. |
| 2004/0167374 A1 | 8/2004 | Schweich et al. |
| 2004/0167539 A1 | 8/2004 | Kuehn et al. |
| 2004/0225300 A1 | 11/2004 | Goldfarb et al. |
| 2004/0225304 A1 | 11/2004 | Vidlund et al. |
| 2004/0236353 A1 | 11/2004 | Bain et al. |
| 2004/0236354 A1 | 11/2004 | Seguin |
| 2004/0243229 A1 | 12/2004 | Vidlund et al. |
| 2004/0267083 A1 | 12/2004 | McCarthy |
| 2005/0004668 A1 | 1/2005 | Aklog et al. |
| 2005/0021055 A1 | 1/2005 | Toubia et al. |
| 2005/0021056 A1 | 1/2005 | St. Goar |
| 2005/0021057 A1 | 1/2005 | St. Goar |
| 2005/0033446 A1 | 2/2005 | Deem et al. |
| 2005/0044365 A1 | 2/2005 | Bachman |
| 2005/0065396 A1 | 3/2005 | Mortier et al. |
| 2005/0075723 A1 | 4/2005 | Schroeder et al. |
| 2005/0075727 A1 | 4/2005 | Wheatley |
| 2005/0101975 A1 | 5/2005 | Nguyen et al. |
| 2005/0125011 A1 | 6/2005 | Spence et al. |
| 2005/0131277 A1 | 6/2005 | Schweich, Jr. |
| 2005/0131533 A1 | 6/2005 | Alfieri et al. |
| 2005/0143620 A1 | 6/2005 | Mortier et al. |
| 2005/0148815 A1 | 7/2005 | Mortier et al. |
| 2005/0149014 A1 | 7/2005 | Hauck et al. |
| 2005/0154402 A1 | 7/2005 | Sauer et al. |
| 2005/0165419 A1 | 7/2005 | Sauer et al. |
| 2005/0171601 A1 | 8/2005 | Cosgrove |
| 2005/0216039 A1 | 9/2005 | Lederman |
| 2005/0240202 A1 | 10/2005 | Shennib et al. |
| 2005/0251187 A1 | 11/2005 | Beane et al. |
| 2006/0020275 A1 | 1/2006 | Goldfarb et al. |
| 2006/0036317 A1 | 2/2006 | Vidlund et al. |
| 2006/0041306 A1 | 2/2006 | Vidlund et al. |
| 2006/0052868 A1 | 3/2006 | Mortier et al. |
| 2006/0058871 A1 | 3/2006 | Zakay et al. |
| 2006/0074484 A1 | 4/2006 | Huber |
| 2006/0074485 A1 | 4/2006 | Realyvasquez |
| 2006/0089671 A1 | 4/2006 | Goldfarb et al. |
| 2006/0100699 A1 | 5/2006 | Vidlund et al. |
| 2006/0127509 A1 | 6/2006 | Eckman |
| 2006/0135993 A1 | 6/2006 | Seguin |
| 2006/0149123 A1 | 7/2006 | Vidlund et al. |
| 2006/0161040 A1 | 7/2006 | McCarthy |
| 2006/0161193 A1 | 7/2006 | Beane et al. |
| 2006/0184203 A1 | 8/2006 | Martin et al. |
| 2006/0195012 A1 | 8/2006 | Mortier et al. |
| 2006/0195134 A1 | 8/2006 | Crittenden |
| 2006/0195183 A1 | 8/2006 | Navia et al. |
| 2006/0241340 A1 | 10/2006 | Vidlund |
| 2006/0287657 A1 | 12/2006 | Bachman |

(56) References Cited

U.S. PATENT DOCUMENTS

| | | |
|---|---|---|
| 2007/0002627 A1 | 1/2007 | Youn |
| 2007/0027451 A1 | 2/2007 | Desinger et al. |
| 2007/0049952 A1 | 3/2007 | Weiss |
| 2007/0050022 A1 | 3/2007 | Vidlund et al. |
| 2007/0055303 A1 | 3/2007 | Vidlund et al. |
| 2007/0088375 A1 | 4/2007 | Beane et al. |
| 2007/0100356 A1 | 5/2007 | Lucatero et al. |
| 2007/0112244 A1 | 5/2007 | McCarthy |
| 2007/0118154 A1 | 5/2007 | Crabtree |
| 2007/0118155 A1 | 5/2007 | Goldfarb et al. |
| 2007/0129737 A1 | 6/2007 | Goldfarb et al. |
| 2007/0179511 A1 | 8/2007 | Paolitto |
| 2007/0197858 A1 | 8/2007 | Goldfarb et al. |
| 2007/0203391 A1 | 8/2007 | Bloom et al. |
| 2007/0232941 A1 | 10/2007 | Rabinovich |
| 2007/0239272 A1 | 10/2007 | Navia et al. |
| 2007/0265643 A1 | 11/2007 | Beane et al. |
| 2007/0299468 A1 | 12/2007 | Viola |
| 2008/0004485 A1 | 1/2008 | Moreschi |
| 2008/0027468 A1 | 1/2008 | Fenton |
| 2008/0051703 A1 | 2/2008 | Thornton et al. |
| 2008/0065011 A1 | 3/2008 | Marchand et al. |
| 2008/0065156 A1 | 3/2008 | Hauser et al. |
| 2008/0065205 A1 | 3/2008 | Nguyen et al. |
| 2008/0091059 A1 | 4/2008 | Machold |
| 2008/0091264 A1 | 4/2008 | Machold |
| 2008/0097482 A1 | 4/2008 | Bain et al. |
| 2008/0097489 A1 | 4/2008 | Goldfarb et al. |
| 2008/0109069 A1 | 5/2008 | Coleman et al. |
| 2008/0125860 A1* | 5/2008 | Webler ............ A61B 17/00234 623/2.36 |
| 2008/0125861 A1 | 5/2008 | Webler et al. |
| 2008/0167714 A1 | 7/2008 | St. Goar |
| 2008/0183194 A1 | 7/2008 | Goldfarb et al. |
| 2008/0188873 A1 | 8/2008 | Speziali |
| 2008/0195200 A1 | 8/2008 | Vidlund et al. |
| 2008/0208006 A1 | 8/2008 | Farr |
| 2008/0228223 A1 | 9/2008 | Alkhatib |
| 2008/0243245 A1 | 10/2008 | Thamber et al. |
| 2009/0105729 A1 | 4/2009 | Zentgraf |
| 2009/0105751 A1 | 4/2009 | Zentgraf |
| 2009/0131880 A1 | 5/2009 | Speziali et al. |
| 2009/0156995 A1 | 6/2009 | Martin et al. |
| 2009/0163934 A1 | 6/2009 | Raschdorf, Jr. |
| 2009/0192598 A1 | 7/2009 | Lattouf et al. |
| 2009/0259304 A1 | 10/2009 | O'Beirne et al. |
| 2010/0030061 A1 | 2/2010 | Canfield et al. |
| 2010/0042147 A1 | 2/2010 | Janovsky et al. |
| 2010/0160726 A1 | 6/2010 | Windheuser |
| 2010/0174297 A1 | 7/2010 | Speziali |
| 2010/0185172 A1* | 7/2010 | Fabro ................ A61B 1/00078 604/500 |
| 2010/0217283 A1 | 8/2010 | St. Goar |
| 2010/0298929 A1* | 11/2010 | Thornton ......... A61B 17/00234 623/2.1 |
| 2011/0011917 A1* | 1/2011 | Loulmet ............ A61B 17/0401 227/181.1 |
| 2012/0184971 A1 | 7/2012 | Zentgraf et al. |
| 2013/0035757 A1 | 2/2013 | Zentgraf et al. |
| 2013/0150710 A1 | 6/2013 | Zentgraf et al. |
| 2014/0039324 A1 | 2/2014 | Speziali |

FOREIGN PATENT DOCUMENTS

| | | |
|---|---|---|
| EP | 1845861 A2 | 10/2007 |
| EP | 1408850 B1 | 9/2009 |
| JP | 06142114 | 5/1994 |
| JP | 2004-531337 | 10/2004 |
| JP | 2007-535342 | 12/2007 |
| WO | WO 1999/00059 A1 | 1/1999 |
| WO | WO 1999/30647 A1 | 6/1999 |
| WO | WO 2000/06026 A2 | 2/2000 |
| WO | WO 2000/06027 A2 | 2/2000 |
| WO | WO 2000/06028 A1 | 2/2000 |
| WO | WO 2000/16700 A1 | 3/2000 |
| WO | WO 2001/66018 A1 | 9/2001 |
| WO | WO 2001/95809 A1 | 12/2001 |
| WO | WO 2003/001893 A2 | 1/2003 |
| WO | WO 2003/059209 A2 | 7/2003 |
| WO | WO 2003/082157 A2 | 10/2003 |
| WO | WO 2003/082158 A1 | 10/2003 |
| WO | WO 2004/021893 A1 | 3/2004 |
| WO | WO 2004/043265 A2 | 5/2004 |
| WO | WO 2005/039428 A2 | 5/2005 |
| WO | WO 2005/087140 A1 | 9/2005 |
| WO | WO 2005/094525 A2 | 10/2005 |
| WO | WO 2006/012750 A1 | 2/2006 |
| WO | WO 2006/032051 A2 | 3/2006 |
| WO | WO 2006/065966 A2 | 6/2006 |
| WO | WO 2006/078694 A2 | 7/2006 |
| WO | WO 2006/116310 A2 | 11/2006 |
| WO | WO 2006/127509 A2 | 11/2006 |
| WO | WO 2007/002627 A1 | 1/2007 |
| WO | WO 2007/027451 A2 | 3/2007 |
| WO | WO 2007/062128 A2 | 5/2007 |
| WO | WO 2007/081418 A1 | 7/2007 |
| WO | WO 2007/117612 A1 | 10/2007 |
| WO | WO 2008/010738 A2 | 1/2008 |
| WO | WO 2009/052528 A2 | 4/2009 |
| WO | WO 2011/070477 A1 | 6/2011 |
| WO | WO 2011/137336 A1 | 11/2011 |
| WO | WO 2012/167120 A2 | 12/2012 |

OTHER PUBLICATIONS

Machine translation of JP 06142114.
Port Access System for Mitral Valve Repair Proves Its Value in Study; MedGadget Jul. 9, 2009 (2 pages).
PCT/US2012/040512, filed Jun. 1, 2012, Written Opinion dated Dec. 21, 2012, 5 pages.
PCT/US2012/040512, filed Jun. 1, 2012, Search Report dated Dec. 21, 2012, 6 pages.
PCT/US2012/067563, International Preliminary Examination Report, dated Jun. 3, 2014, 9 pages.
Extended European Search Report, EP 06718728.6, dated Nov. 11, 2009, 7 pages.
PCT International Preliminary Report on Patentability for PCT/US2008/080560, dated Apr. 29, 2010, 7 pages.
PCT International Search Report and Written Opinion, PCT/US06/01699, dated May 6, 2008, 5 pages.
European Search Report, EP 08839048.9, dated Sep. 16, 2010, 7 pages.
PCT International Search Report, PCT/US2008/080560, dated Aug. 25, 2009, 3 pages.
PCT/US2011/067884, Search Report/Written Opinion dated Jul. 30, 2011, 11 pages.
EP Application No. 12792116.1, Extended Search Report dated Jan. 8, 2015, 7 pages.
JP Application No. 2014-513757, Notification of Refusal dated Mar. 7, 2016, translation as obtained through Global Dossier, 3 pages.
AU Application No. 2012261998, Patent Examination Report No. 1, dated Mar. 3, 2016, 4 pages.
CN Application No. 201280038285.7, First Office Action dated Aug. 4, 2015, translation as obtained through Global Dossier, 6 pages.
Application and File History for U.S. Appl. No. 11/813,695, filed Jul. 11, 2007, now U.S. Pat. No. 8,465,500. Inventor: Speziali.
Application and File History for U.S. Appl. No. 12/254,808, filed Oct. 20, 2008. Inventor: Zentgraf.
Application and File History for U.S. Appl. No. 12/254,807, filed Oct. 20, 2008, now U.S. Pat. No. 8,758,393. Inventor: Zentgraf.
Application and File History for U.S. Appl. No. 12/709,220, filed Feb. 19, 2010. Inventor: Speziali.
Application and File History for U.S. Appl. No. 13/898,709, filed May 21, 2013. Inventor: Speziali.
Application and File History for U.S. Appl. No. 13/339,865, filed Dec. 29, 2011. Inventors: Zentgraf et al.
Application and File History for U.S. Appl. No. 13/340,185, filed Dec. 29, 2011. Inventors: Zentgraf et al.

(56) References Cited

OTHER PUBLICATIONS

Application and File History for U.S. Appl. No. 13/486,632, filed Jun. 1, 2012. Inventor Zentgraf et al.
Application and File History for U.S. Appl. No. 13/692,027, filed Dec. 3, 2012. Inventors: Zentgraf et al.
Application and File History for U.S. Appl. No. 14/310,069, filed Jun. 20, 2014. Inventor: Zentgraf.
EP Application No. 12792116.1, Communication Pursuant to Article 94(3) EPC, dated May 24, 2018, 7 pages.
Canadian Application No. 2,837,206, Office Action dated Apr. 18, 2018, 3 pages.

* cited by examiner

MINIMALLY INVASIVE REPAIR OF HEART VALVE LEAFLETS

RELATED APPLICATION

This application is a continuation of application Ser. No. 13/486,632 filed Jun. 1, 2012, which claims the benefit of U.S. Provisional Application No. 61/492,135 filed Jun. 1, 2011, each of which is hereby incorporated herein by reference.

FIELD OF THE INVENTION

The present invention relates to minimally invasive delivery of a suture. More particularly, the present invention relates to attaching the suture as an artificial chordae tendineae to a flailing or prolapsing leaflet in a beating heart via an intravascular ventricular septal approach.

BACKGROUND OF THE INVENTION

Various types of surgical procedures are currently performed to investigate, diagnose, and treat diseases of the heart and the great vessels of the thorax. Such procedures include repair and replacement of mitral, aortic, and other heart valves, repair of atrial and ventricular septal defects, pulmonary thrombectomy, treatment of aneurysms, electrophysiological mapping and ablation of the myocardium, and other procedures in which interventional devices are introduced into the interior of the heart or a great vessel.

Using current techniques, many of these procedures require a gross thoracotomy, usually in the form of a median sternotomy, to gain access into the patient's thoracic cavity. A saw or other cutting instrument is used to cut the sternum longitudinally, allowing two opposing halves of the anterior or ventral portion of the rib cage to be spread apart. A large opening into the thoracic cavity is thus created, through which the surgical team may directly visualize and operate upon the heart and other thoracic contents.

Surgical intervention within the heart by a thoracotomy generally requires isolation of the heart and coronary blood vessels from the remainder of the arterial system, and arrest of cardiac function (an "open heart" procedure). Usually, the heart is isolated from the arterial system by introducing an external aortic cross-clamp through a sternotomy and applying it to the aorta between the brachiocephalic artery and the coronary ostia. Cardioplegic fluid is then injected into the coronary arteries, either directly into the coronary ostia or through a puncture in the aortic root, so as to arrest cardiac function. In some cases, cardioplegic fluid is injected into the coronary sinus for retrograde perfusion of the myocardium. The patient is placed on cardiopulmonary bypass to maintain peripheral circulation of oxygenated blood.

Of particular interest to the present invention are open heart procedures for surgical treatment of heart valves, especially the mitral and aortic valves. According to recent estimates, more than 79,000 patients are diagnosed with aortic and mitral valve disease in U.S. hospitals each year. More than 49,000 mitral valve or aortic valve replacement procedures are performed annually in the U.S., along with a significant number of heart valve repair procedures.

Various surgical techniques may be used during an open heart procedure to repair a diseased or damaged valve, including annuloplasty (contracting the valve annulus), quadrangular resection (narrowing the valve leaflets), commissurotomy (cutting the valve commissures to separate the valve leaflets), shortening mitral or tricuspid valve chordae tendonae, reattachment of severed mitral or tricuspid valve chordae tendonae or papillary muscle tissue, and decalcification of valve and annulus tissue. Alternatively, the valve may be replaced by excising the valve leaflets of the natural valve and securing a replacement valve in the valve position, usually by suturing the replacement valve to the natural valve annulus. Various types of replacement valves are in current use, including mechanical and biological prostheses, homografts, and allografts.

The mitral valve, located between the left atrium and left ventricle of the heart, is most easily reached through the wall of the left atrium, which normally resides on the posterior side of the heart, opposite the side of the heart that is exposed by a median sternotomy. Therefore, to access the mitral valve via a sternotomy, the heart is rotated to bring the left atrium into a position accessible through the sternotomy. An opening, or atriotomy, is then made in the left atrium, anterior to the right pulmonary veins. The atriotomy is retracted by means of sutures or a retraction device, exposing the mitral valve directly posterior to the atriotomy. One of the aforementioned techniques may then be used to repair or replace the valve.

An alternative technique for mitral valve access during an open heart procedure may be used when a median sternotomy and/or rotational manipulation of the heart are/is undesirable. In this technique, a large incision is made in the right lateral side of the chest, usually in the region of the fifth intercostal space. One or more ribs may be removed from the patient, and other ribs near the incision are retracted outward to create a large opening onto the thoracic cavity. The left atrium is then exposed on the posterior side of the heart, and an atriotomy is formed in the wall of the left atrium, through which the mitral valve may be accessed for repair or replacement.

The mitral and tricuspid valves inside the human heart include an orifice (annulus), two (for the mitral) or three (for the tricuspid) leaflets and a subvalvular apparatus. The subvalvular apparatus includes multiple chordae tendineae, which connect the mobile valve leaflets to muscular structures (papillary muscles) inside the ventricles. Rupture or elongation of the chordae tendineae results in partial or generalized leaflet prolapse, which causes mitral (or tricuspid) valve regurgitation. A commonly used technique to surgically correct mitral valve regurgitation is the implantation of artificial chordae (usually 4-0 or 5-0 Gore-Tex sutures) between the prolapsing segment of the valve and the papillary muscle. This open heart operation is generally carried out through a median sternotomy and requires cardiopulmonary bypass with aortic cross-clamp and cardioplegic arrest of the heart.

Using such open heart techniques, the large opening provided by a median sternotomy or right thoracotomy enables the surgeon to see the mitral valve directly through the left atriotomy, and to position his or her hands within the thoracic cavity in close proximity to the exterior of the heart for manipulation of surgical instruments, removal of excised tissue, and/or introduction of a replacement valve through the atriotomy for attachment within the heart. However, these invasive open heart procedures produce a high degree of trauma, a significant risk of complications, an extended hospital stay, and a painful recovery period for the patient. Moreover, while heart valve surgery produces beneficial results for many patients, numerous others who might benefit from such surgery are unable or unwilling to undergo the trauma and risks of current techniques.

One alternative to open heart surgery is a robotically guided, thoracoscopically assisted cardiotomy procedure marketed under the tradename of the DaVinci® system. Instead of requiring a sternotomy, the DaVinci® system uses a minimally invasive approach guided by camera visualization and robotic techniques. Unfortunately, the DaVinci® system is not approved for mitral valve repair procedures on a beating heart. Thus, the use of the DaVinci® system for mitral valve repair still requires a cardiopulmonary bypass with aortic cross-clamp and cardioplegic arrest of the heart.

While there are other laparoscopic and minimally invasive surgical techniques and tools that have been developed, none of these devices are useable for the unique requirements of mitral valve repair on a beating heart. Suturing devices like the Superstich™ vascular suturing device or the Gore® suture passer are designed to permit manual placement of sutures as part of a surgical procedure, but are not designed for use on a beating heart. While certain annuloplasty techniques and instruments that can suture an annuloplasty ring as part of vascular repair or heart bypass surgery may be used in conjunction with a beating heart, these annuloplasty procedures do not involve the capture or retention of a constantly moving leaflet. Consequently, the design and use of annuloplasty techniques and instruments are of little help in solving the problems of developing instruments and techniques for minimally invasive thoracoscopic repair of heart valves during a beating heart procedure.

Recently, a technique has been developed for minimally invasive thoracoscopic repair of heart valves while the heart is still beating. Int'l Pub. No. WO 2006/078694 A2 to Speziali, which is incorporated by reference herein, discloses a thoracoscopic heart valve repair method and apparatus. Instead of requiring open heart surgery on a stopped heart, the thorascopic heart valve repair methods and apparatus taught by Speziali utilize fiber optic technology in conjunction with transesophageal echocardiography (TEE) as a visualization technique during a minimally invasive surgical procedure that can be utilized on a beating heart. U.S. Publication No. 2008/0228223 to Alkhatib also discloses a similar apparatus for attaching a prosthetic tether between a leaflet of a patient's heart valve and another portion of the patient's heart to help prevent prolapse of the leaflet and/or to otherwise improve leaflet function.

More recent versions of these techniques are disclosed in U.S. Patent Application Publication Nos. 2009/0105751 and 2009/0105729 to Zentgraf, which disclose an integrated device that can enter the heart chamber, navigate to the leaflet, capture the leaflet, confirm proper capture, and deliver a suture as part of a mitral valve regurgitation (MR) repair.

These references disclose suturing valve leaflets by accessing the heart through an open surgical approach that requires an artificial opening in the heart wall be made, for example at the apex of the ventricle, during the open surgical approach. It would be advantageous for a minimally invasive suture delivery system to be able to suture valve leaflets in a beating heart procedure without requiring an open surgical approach or an incision into the exterior ventricular wall in order to minimize blood loss.

SUMMARY OF THE INVENTION

Embodiments of the present invention allow for repair of heart valve regurgitation during a beating heart procedure including various steps and apparatuses for entering the heart chamber, navigating to a heart valve leaflet, capturing the leaflet, confirming proper capture, and delivering a suture. The devices and procedures of these embodiments can be used with an intravascular catheter based approach for delivery of sutures for the treatment of heart valve regurgitation.

In one embodiment, the system provides venous access into a heart chamber (venous access via the femoral or jugular vein) while minimizing the loss of blood within and without the system. The device can be inserted through the right atrium and into the right ventricle, with the position within the ventricular apex visualized via ultrasound or fluoroscopy. Once access into the heart chamber is achieved, the system is positioned via a non-invasive imaging modality. The system allows capture of intra-cardiac tissue structure. Once captured, the system allows control to be maintained over said tissue structure. Imaging modalities allow confirmation of proper capture position of the system relative to the tissue structure. The system then accommodates the delivery of the deployment catheter to said tissue structure once proper position has been confirmed.

In one embodiment, a guide-in-guide catheter system provides venous access to the ventricular septal wall for a trans-septal puncture tool to provide the access to the left ventricular cavity. Once the left ventricle is accessed, an internal guide catheter can be advanced within the external guide across the septal wall into the left ventricle. The external guide catheter can have a side exiting lumen to facilitate the positioning of the internal guide, or alternatively a septal puncture catheter with a septal puncture device therein, to the selected area for crossing the ventricular septum. A curve in the guide can angle the tip of the catheter to the desired location for trans-septal puncture. A guide wire may be used to maintain position. After the septal puncture is completed the device can be removed and a dilator inserted into the internal guide to aid the passage of the guide through the septal wall. The dilator can be removed after the internal guide has crossed the septal wall. The internal guide can also have a pre-shaped curvature to the distal tip. This curve can provide the direction support to guide the deployment catheter toward the mitral valve.

The deployment catheter can have a central lumen to accept a guide wire used in positioning the deployment catheter to effectively engage the mitral valve. The central lumen can also be used for an intravascular ultrasound device or a direct visualization device. The suture is deployed by the deployment catheter at the selected site. The deployment catheter can be withdrawn from the guide catheter and re-loaded or replaced for successive suture deployments.

In one embodiment, a medical repair device may be added to the procedure, such as a leaflet extension, a passive valve occlusion device or a pledget. The deployed sutures exit the internal guide catheter and can be temporarily fixed outside the body. Once the desired amount of sutures is positioned, they can be loaded through a central lumen of a septal seal device. The septal seal device is advanced through the external guide catheter and guided, via the sutures and external guide catheter, through the ventricular puncture site. The right ventricular side of the seal device is deployed and then the left side of the seal device is deployed. The internal catheter is then detached from the septal seal element and withdrawn from the external guide catheter. The sutures remain in the internal lumen of the septal closure device attached to the mitral valve and exit through the external guide.

In one embodiment, the sutures can have the tension individually adjusted to evaluate the physiological effect. The evaluation can be done using transesophageal echocardiography or other non-invasive methods. If the suture is overly tightened, a catheter can be delivered through the external guide to the lumen seal inside of the septal seal device. Advancing the catheter through the seal will release suture tension and allow for re-tensioning. When the tensioning task is complete, the sutures can be fixed at the septal seal element.

In one embodiment, an anchor catheter with a distally mounted cam lock element or other mechanical lock permanently fixes to the septal seal element and fixes the position of the sutures while maintaining the adjusted tension. This step completes the septal seal and suture tensioning. The anchor catheter can then be withdrawn with the proximal ends of the sutures. The sutures can then be threaded through the lumen or opening of a cutting catheter. A cutting catheter can be advanced over the sutures until it contacts the septal seal device. The cutting catheter then cuts the sutures at the seal to complete the implant procedure. The entire catheter system is then removed from the patient and the access site closed.

In another embodiment, a deployment catheter is capable of multiple suture deployments in a single activation. This would reduce the number of instrument exchanges and provide increased control of the position of the sutures relative to each other.

A further embodiment uses the sutures to deliver a biomatrix patch to enhance closure. The patch can be attached to the valve with the sutures. The patch could be delivered to either the ventricular or atrial side of the mitral valve leaflet. This patch can improve leaflet coaptation and reduce/eliminate mitral valve regurgitation by augmenting the native leaflet tissue structure supported by the delivery of a biomatrix material that can support the mitral valve annular ring or subvalvular apparatus.

Another embodiment includes the deployment of a passive occlusive device intended to improve valve closure, the device would be delivered, positioned, and anchored via the ventricular septal approach described herein.

The above summary of the various embodiments of the invention is not intended to describe each illustrated embodiment or every implementation of the invention. This summary represents a simplified overview of certain aspects of the invention to facilitate a basic understanding of the invention and is not intended to identify key or critical elements of the invention or delineate the scope of the invention.

BRIEF DESCRIPTION OF DRAWINGS

The embodiments of the present invention may be more completely understood in consideration of the following detailed description of various embodiments in connection with the accompanying drawings, in which.

Figure 2A:
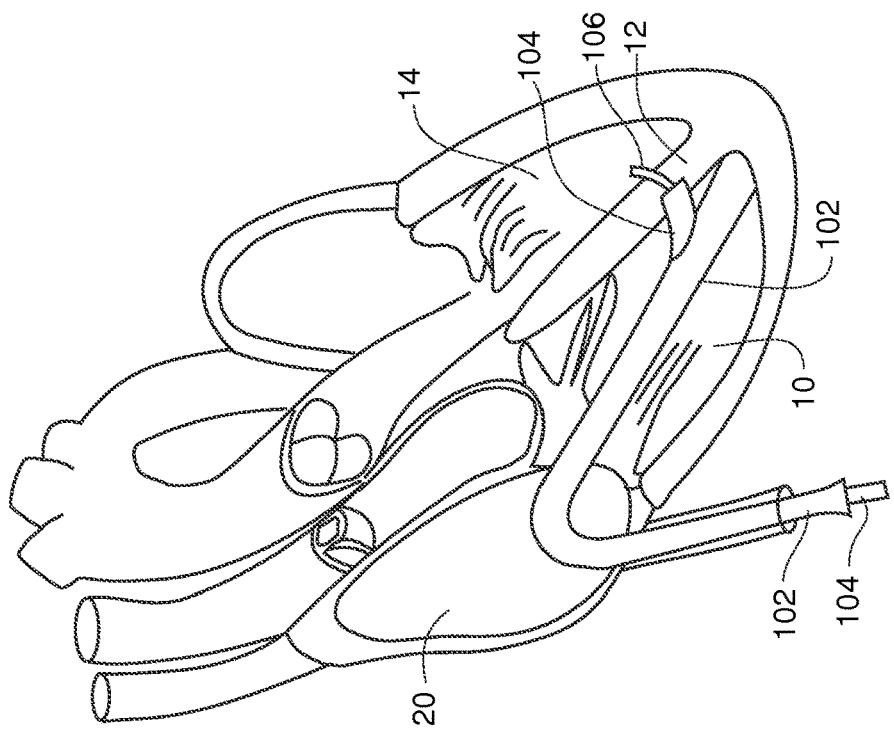
FIG. 2A is a view of a valve leaflet repair device according to an embodiment of the present invention with an internal guide and puncture tool passed into the left ventricle.

While the present invention is amenable to various modifications and alternative forms, specifics thereof have been shown by way of example in the drawings and will be described in detail. It should be understood, however, that the intention is not to limit the present invention to the particular embodiments described. On the contrary, the invention is to cover all modifications, equivalents, and alternatives falling within the spirit and scope of the present invention.

DESCRIPTION OF EMBODIMENTS

In the following detailed description of the present invention, numerous specific details are set forth in order to provide a thorough understanding of the present invention. However, one skilled in the art will recognize that various embodiments of the present invention may be practiced without these specific details. In other instances, well-known methods, procedures, and components have not been described in detail so as to not unnecessarily obscure aspects of the present invention.

One embodiment of the heart valve repair and delivery system will be examined to demonstrate the multiple catheter access steps required to enter the target heart chamber and deliver the repair device. This embodiment performs the repair of mitral valve regurgitation by delivering sutures to repair the defective valve with a deployment catheter that acts to reduce/eliminate mitral valve regurgitation (MR). In other embodiments, the access approach described herein can be used to access the heart for any other type of procedure, such as, for example, a heart valve replacement, repair of another heart structure or delivery of repair devices other than sutures to valve leaflets.

Figure 1:
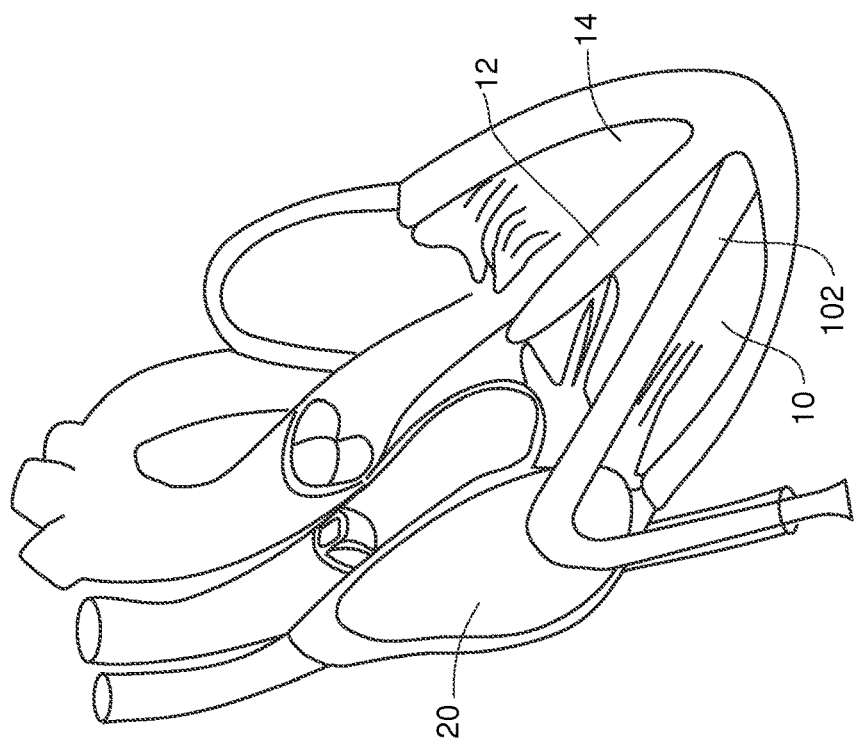
FIG. 1 is a view of a device for venous access into a heart chamber via the femoral vein to facilitate repair of a heart valve leaflet according to an embodiment of the present invention.
Figure 2B:
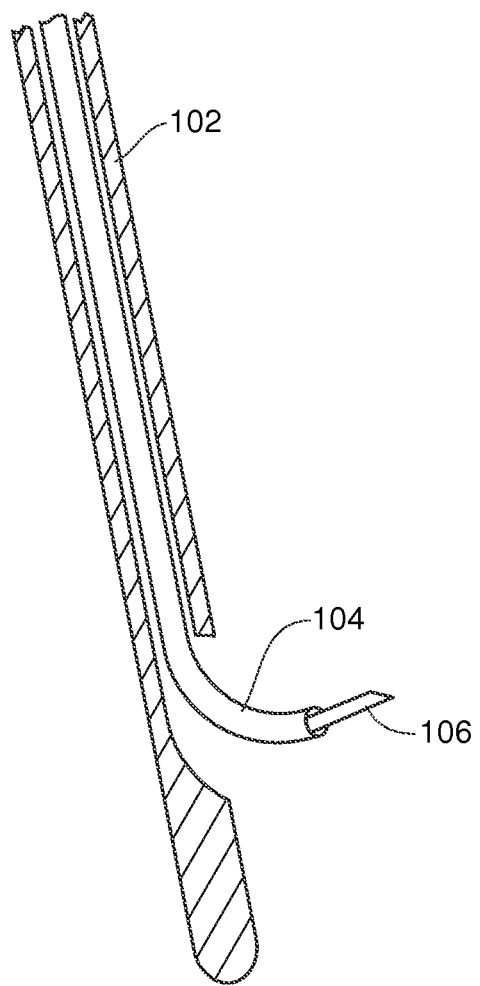
FIG. 2B is a partial view of the valve leaflet repair device depicted in FIG. 2A.

Embodiments of the present invention can be used as a vascular access system. It can include a standard vascular introducer that 1) eliminates the need for multiple passes of the instrument against the vein wall, 2) minimizes blood loss due to instrument leakage (circular components are more amenable to closer tolerances and sealing capability), and 3) reduces push/pull forces on the vein wall. The introducer contains seals to maintain hemostasis during instrument exchanges. A side exiting external guide catheter 102 can provide access into the right ventricle 10 as shown in FIG. 1. In one embodiment, a distal end of the external guide 102 can include a suction element to ensure that it holds its position in the right ventricle at, for example, the right ventricular apex. The system can include an internal guide catheter 104 disposed in the side exiting external guide catheter 102 design that facilitates the access through the right ventricle 10 to the right ventricular wall. The introducer and/or external guide catheter 102 can therefore function as means for accessing the right ventricle. A standard septal puncture tool 106 with a needle like end can serve as a means for creating an opening in the septum to create the hole in the ventricular septal wall 12 to provide the passageway for the guide catheter 104 through the wall as depicted in FIG. 2A. As used herein, the term catheter can refer to an elongate, generally flexible and tubular medical device that extends along a longitudinal axis and defines a diameter around the longitudinal axis.

Figure 4:
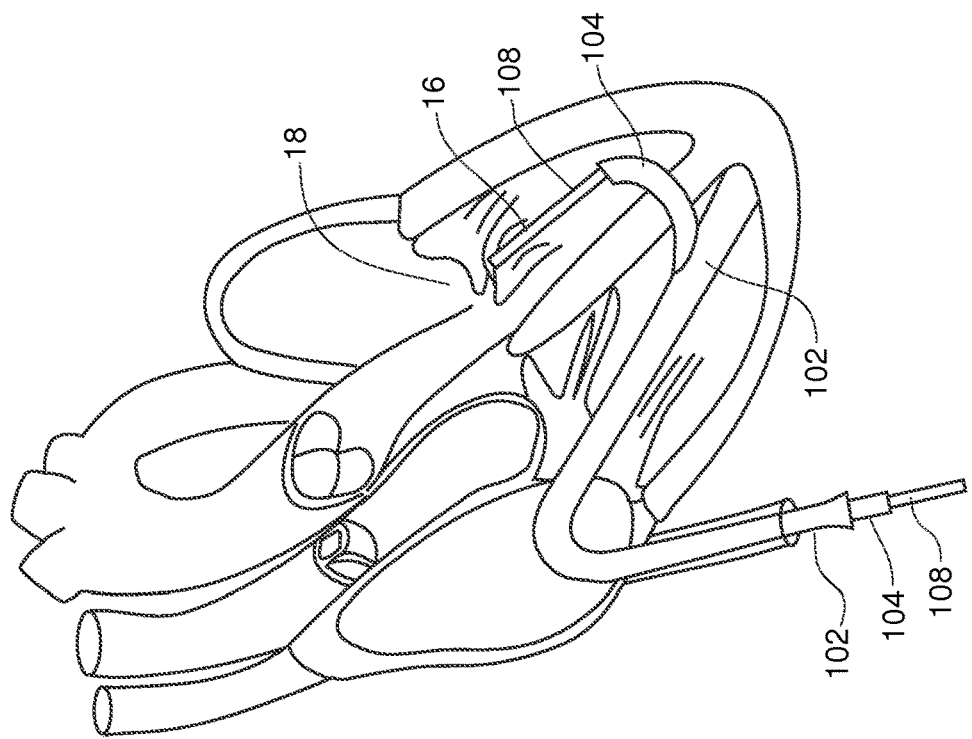
FIG. 4 is a view of a valve leaflet repair device according to an embodiment of the present invention with a deployment catheter exiting an internal guide and positioned at the mitral valve.
Figure 3:
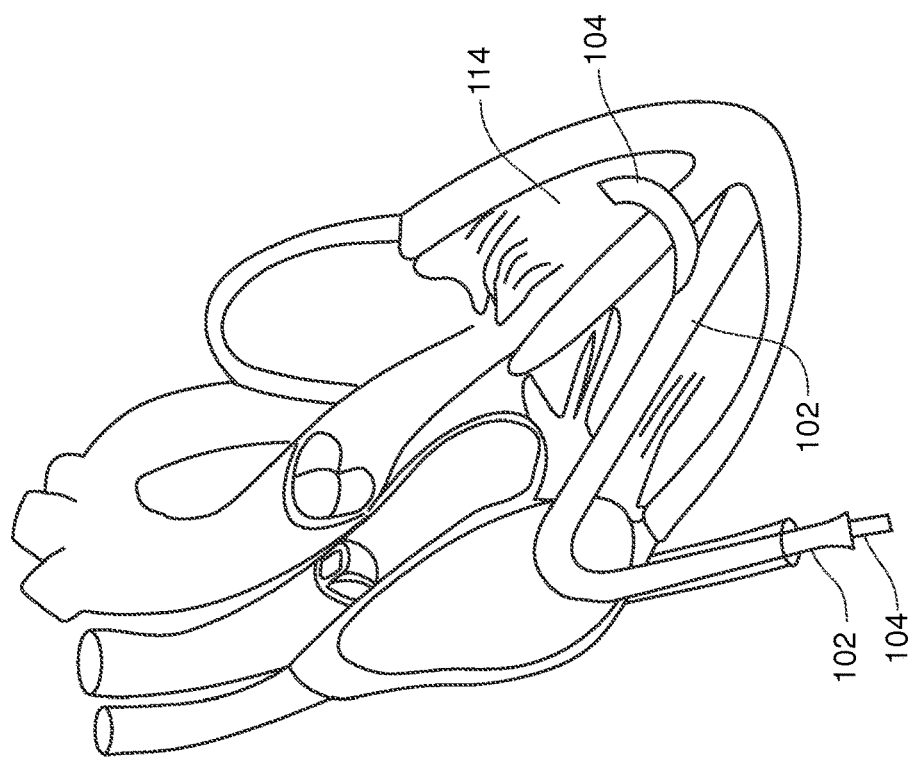
FIG. 3 is a view of a valve leaflet repair device according to an embodiment of the present invention with an internal guide exiting a side exit guide catheter.
Figure 5A:
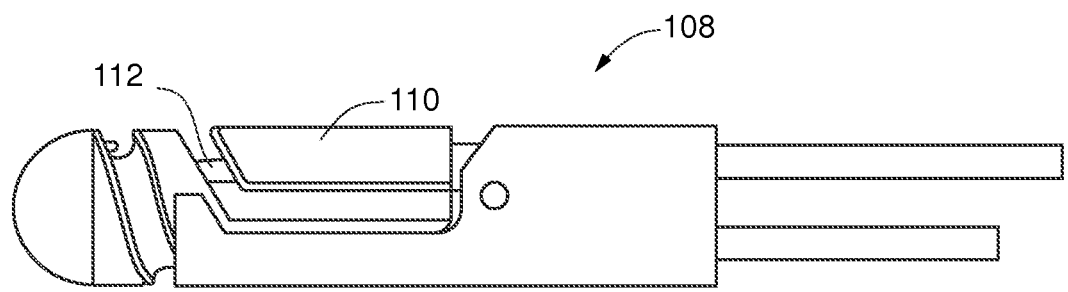
FIG. 5A is a view of a deployment catheter tip according to an embodiment of the present invention with a moveable catheter jaw and a suture capture needle, with the catheter jaw in the closed position.
Figure 5B:
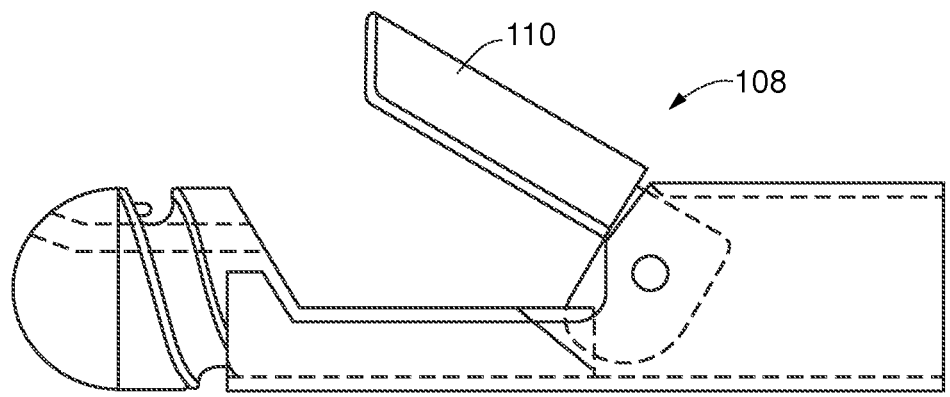
FIG. 5B is a view of the deployment catheter tip of FIG. 5A with the moveable catheter in the open position.
Figure 6:
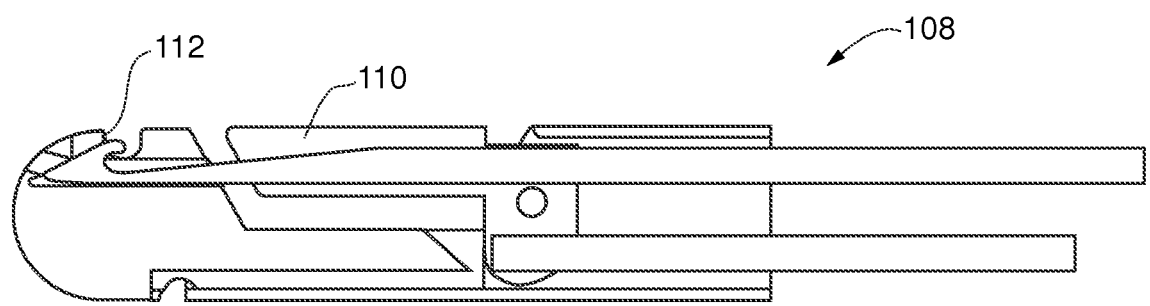
FIG. 6 is a cross-sectional view of the deployment catheter tip of FIGS. 5A and 5B.
Figure 7:
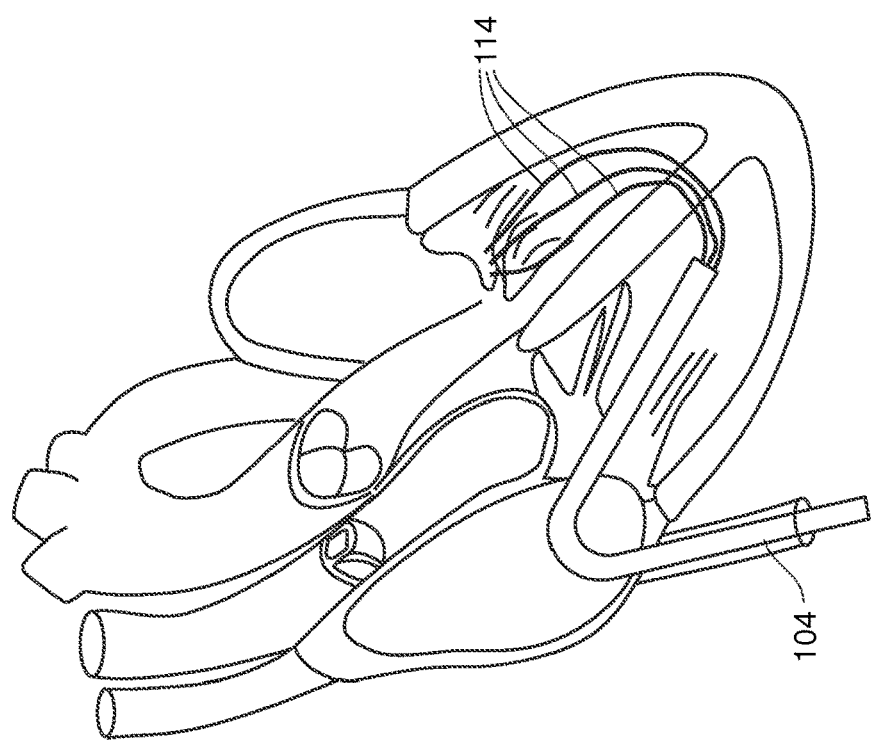
FIG. 7 is a view of a valve leaflet repair device according to an embodiment of the present invention with several sutures attached to the mitral valve and exiting through an internal guide.

The pre-shaped internal guide catheter 104 is then advanced into the left ventricle 14, as shown in FIG. 3, and positioned to deliver a deployment catheter 108 to properly capture a leaflet 16 of the mitral valve 18 for repair as shown in FIG. 4. The internal guide catheter 104 can therefore function as a means for positioning the deployment catheter 108 in the left ventricle. The deployment catheter 108, as shown in FIGS. 5A-5B and 6, can provide a means for deploying a repair device and can include a clamping mechanism 110 or other means for grasping for capturing the leaflet and a suture deployment mechanism including a suture capture needle 112 or other means for inserting the suture into the leaflet. The deployment catheter 108 can be exchangeable within the guide catheter 104 to permit multiple suture 114 deployments on the valve leaflet as shown in FIG. 7. Alternatively, the deployment catheter 108 can deliver several sutures 114 at one deployment. Note that in some Figures, such as FIG. 7, the external guide catheter 102 is not shown for sake of clarity.

As can be seen in FIG. 4, embodiments of the present invention provide a tri-catheter approach for accessing a heart valve to deploy a repair device onto a portion of the valve, such as a valve leaflet. The tri-catheter approach can include the external guide catheter 102, internal guide catheter 104 received within the external guide catheter 102 and deployment catheter 108 received within the internal guide catheter 104. In some embodiments, as depicted in FIG. 4, the tri-catheter arrangement can define a generally S-shaped access configuration to the valve with the catheters defining a first curve in the right atrium to access the right ventricle and a second curve where the internal guide 104 exits the external guide 102 to cross the septum and access the heart valve in the left ventricle. In one embodiment, the external guide 102 defines a curvature of about 130 degrees and the internal guide 104 has a generally U-shaped distal end that angles towards the valve to define the generally S-shaped configuration. Both external guide 102 and internal guide 104 may be given various curvatures to match the anatomy of a given patient. In one embodiment, the external guide 102 has a diameter of between 12 and 16 French and the inner guide 104 has approximately 2 French sizes smaller than the external guide 102. The delivery catheter 108 and other catheters inserted into the internal guide 104 can have a diameter that is approximately 2 French sizes smaller than the internal guide 104.

The deployment catheter 108 can alternatively or additionally deliver an additional medical repair device such as a leaflet extension or a passive valve occlusion device. A medical repair device is a device that is permanently implanted for the repair treatment or a device that supports the primary repair treatment. Such medical repair devices can be suture materials, biomatrix materials used to support or augment a tissue structure, or devices that would provide repair treatment by device assisted coaptation of one of the cardiac valves. In one embodiment, deployment catheter 108 can deliver a pledget, such as described in commonly owned, copending U.S. patent application Ser. No. 13/339,865, which is incorporated by reference herein. In another embodiment, deployment catheter 108 can deliver a replacement valve or a device that seats in the valve annulus and has a portion extending down between the valve leaflets that is anchored to the heart.

Figure 8:
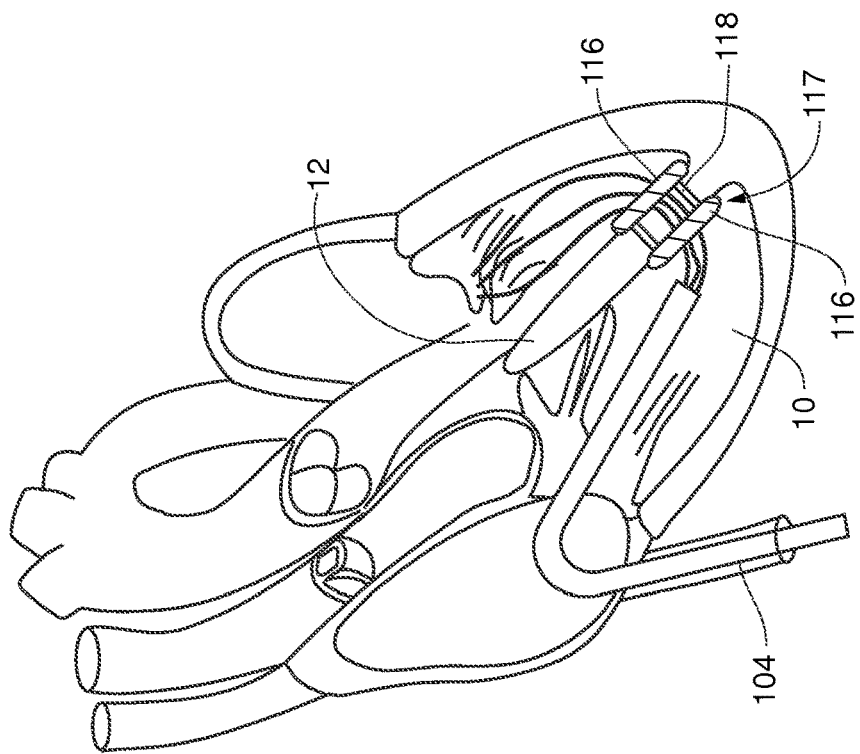
FIG. 8 is a view of a valve leaflet repair device according to an embodiment of the present invention with ventricular septal seal devices deployed in the septal wall with sutures extending through a center lumen.
Figure 9:
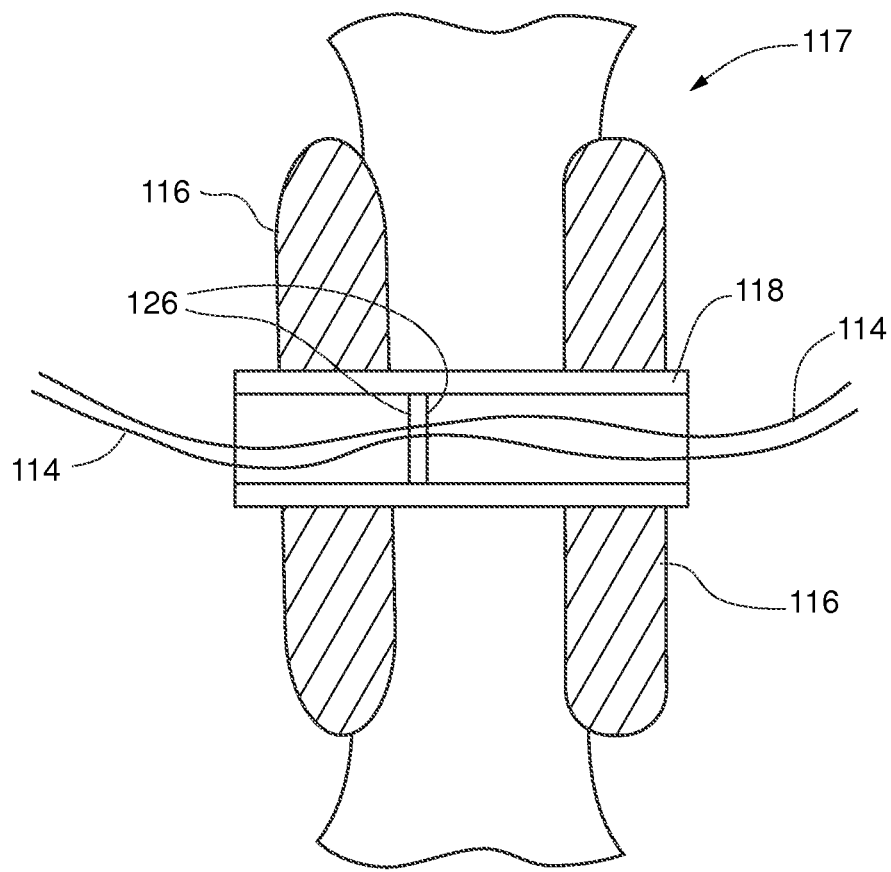
FIG. 9 is a schematic representation of the septal seal device of FIG. 8 in place in the heart.

After the desired number of sutures 114 is deployed, the sutures 114 are threaded through a lumen of a septal seal device 117. The septal sealing device 117 is then advanced down the guide catheter 104 with a seal catheter and into the right ventricle 10. The device 117 is positioned to have right side and left side seal elements 116, depicted in FIG. 9, positioned on opposite sides of the septal wall 12. The sealing elements 116 are deployed to provide a means for sealing the opening in the septum with the sealing device 117 and the catheter withdrawn as shown in FIG. 8. In one embodiment, seal device 117 comprise a pre-shaped wire frame having tensioned flanges on opposing sides that abut the opposing sides of the septal wall 12 to hold the seal elements 116 in place and an internal lumen 118 extending through the device. In one embodiment, the wire frame is comprised of Nitinol.

Figure 10:
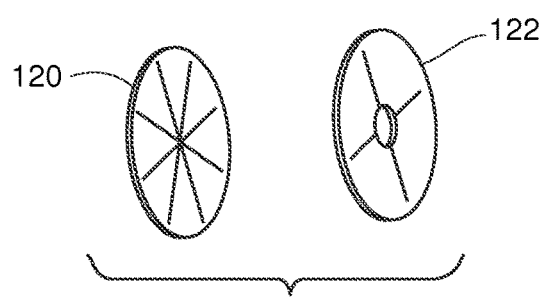
FIG. 10 is a perspective view of septal seal types according to embodiments of the present invention.
Figure 11:
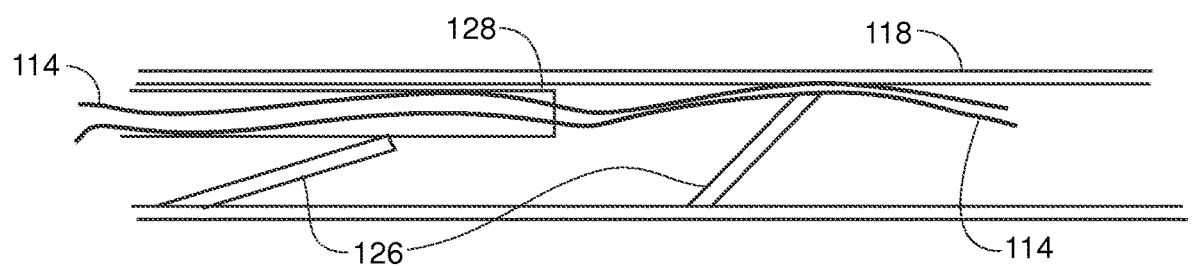
FIG. 11 is a partial view of a septal seal device lumen with a seal element for holding a suture in tension showing the suture freed from tension by a catheter that releases the seal element.

The sutures 114 can now be tensioned from a location external of the heart to have a desired tension that provides for proper valve function. The internal lumen 118 of the septal sealing device 117 can have one or more seals 126 that provide pressure on the sutures to prevent them from easily moving to maintain the set tension on the sutures 114 and provide a means for setting the tension. Seals 126 can also serve to maintain the integrity of the lumen 118. The seal can be similar to a silicone slit seal 122 or a flap seal 120, as shown in FIG. 10, both of which facilitate release of the suture 114 position using a catheter 128 or other means for re-tensioning if desired to allow for re-tensioning, as shown in FIG. 11.

Figure 12:
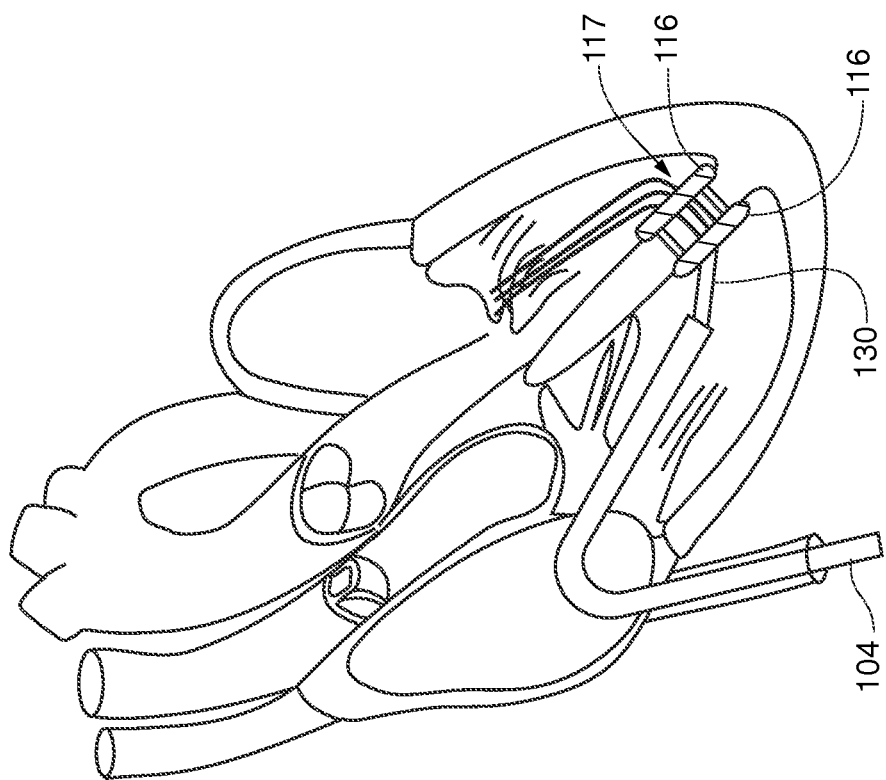
FIG. 12 is a view of a valve leaflet repair device according to an embodiment of the present invention with an anchor device fixing the position of the sutures.
Figure 13:
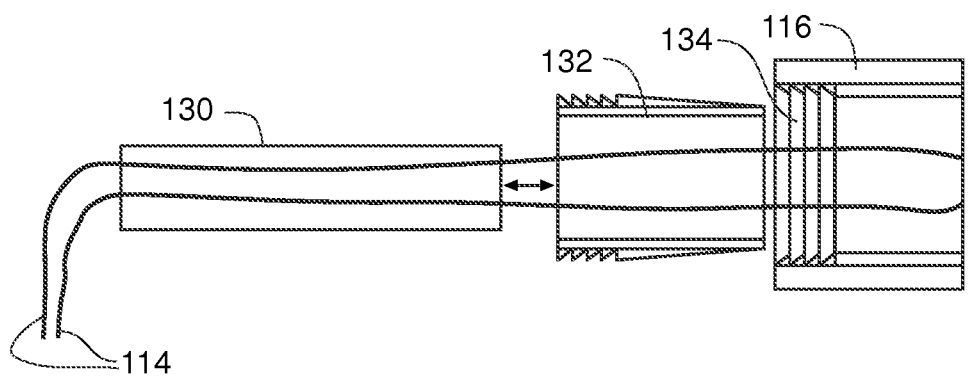
FIG. 13 is a side cut-away view of the anchor device of FIG. 12 having a fixation catheter with a locking element for mating with seal internal lock features.

After tension of the sutures 114 is confirmed via transesophageal echo cardiography, for example, the sutures 114 can be fixed to the sealing device 117 for permanent anchoring of the sutures 114. The sutures 114 are threaded through a lumen in an anchoring catheter 130 to provide coaxial positioning of a locking element 132 or anchoring device that can function as a means for anchoring the sutures at the sealing device 117. Fixation can be accomplished with the anchoring catheter 130 with the releasable locking element 132 that interfaces with internal lock features 134 in the right side sealing element 116 of the sealing device 117 and locks the sutures 114 in position and permanently fixes to the sealing device 117 as shown in FIGS. 12 and 13. The locking mechanism 132 can be a rotational cam lock or a screw in element.

Figure 14:
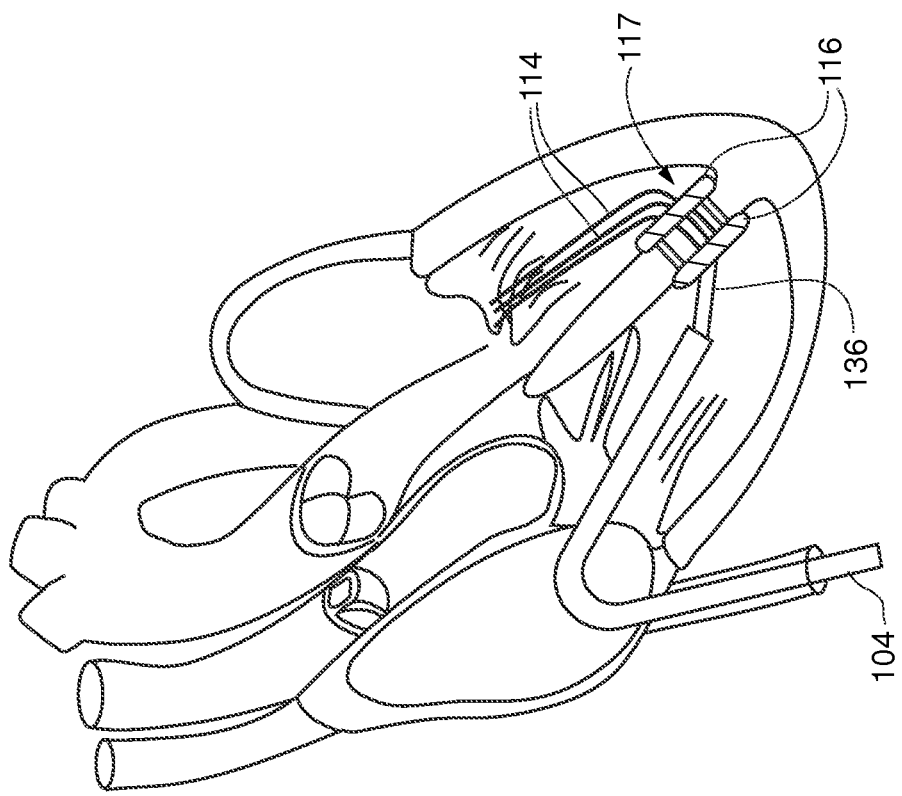
FIG. 14 is a view of a valve leaflet repair device according to an embodiment of the present invention with a cutting device for cutting sutures at the right ventricular side of a septal seal.
Figure 15:
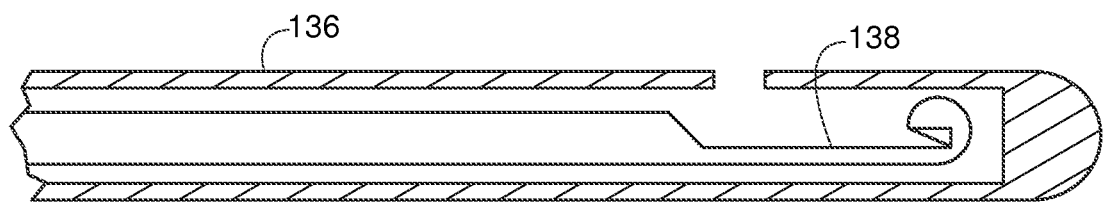
FIG. 15 is a side cross-sectional view of the suture cutting device of FIG. 14.
Figure 16:
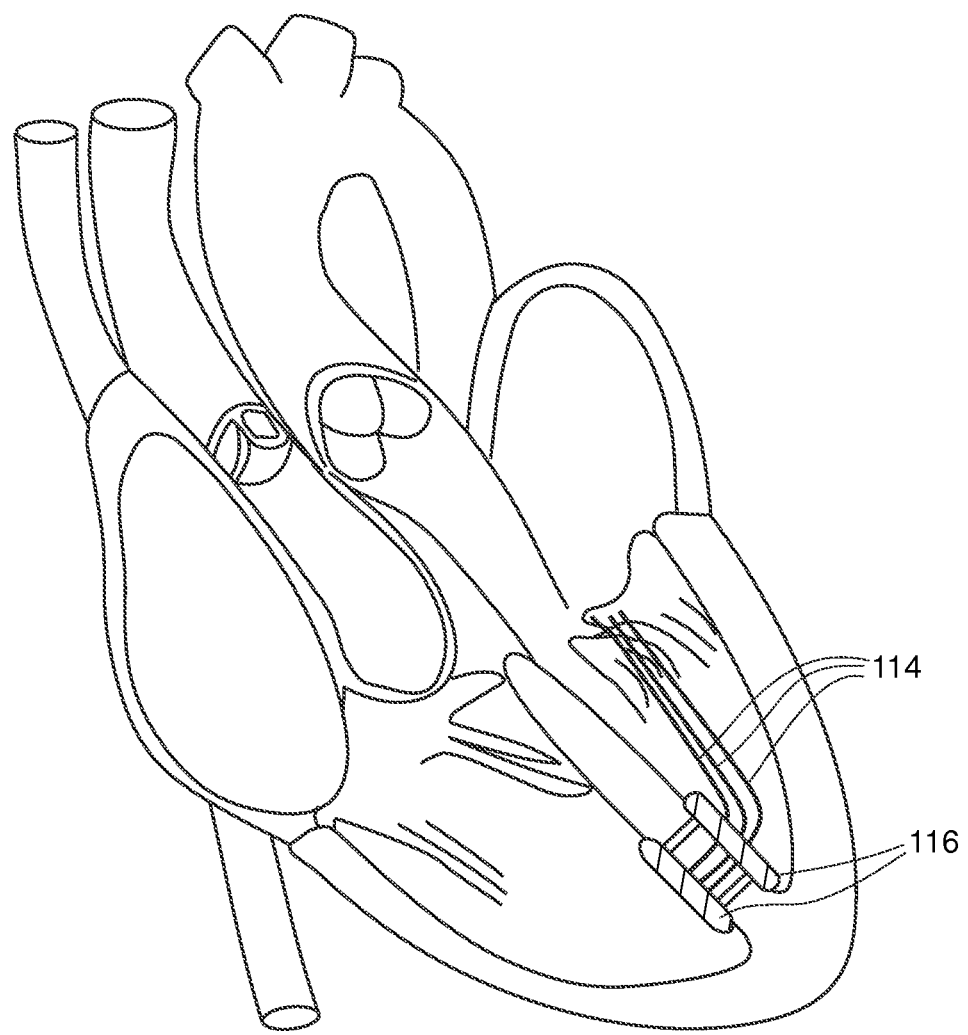
FIG. 16 is a view of a completed implant procedure using a valve leaflet repair device according to an embodiment of the present invention.

Once the sutures 114 are permanently fixed to the sealing element 116, the sutures 114 can be threaded through the end of a cutting catheter 136 which is advanced until it contacts the sealing element 116 as shown in FIG. 14. The sutures 114 can then be cut at the sealing element 116 with a cutting device or tool 138 in the cutting catheter 136, also shown in FIG. 15, which is then withdrawn. The intervention is then complete and the guide catheters and introducers can be withdrawn leaving behind the anchored sutures 114 as shown in FIG. 16. The access site can then be closed.

Figure 17:
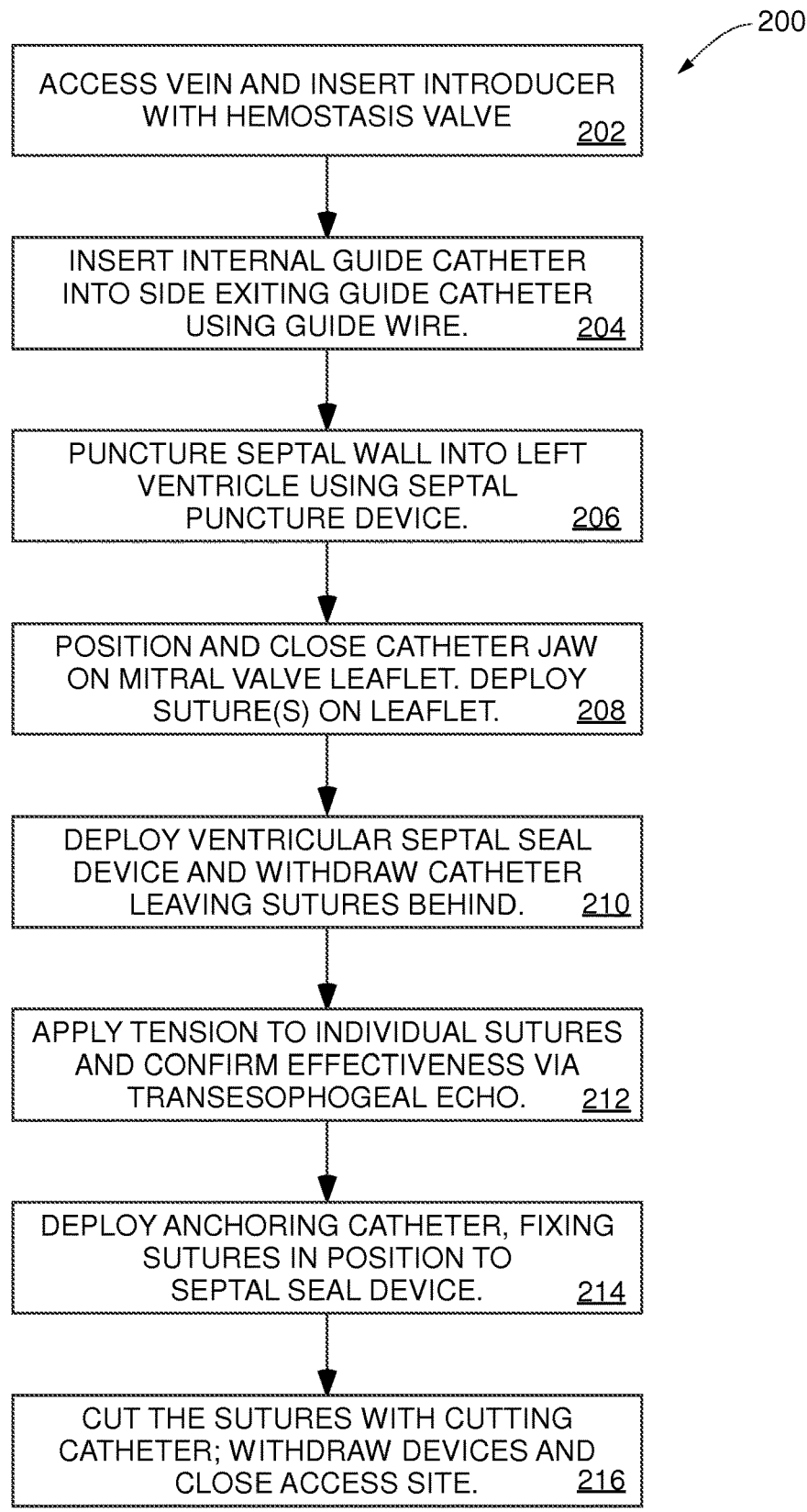
FIG. 17 is a flow chart of surgical procedural steps for repair of heart valve leaflets according to an embodiment of the present invention.

FIG. 17 depicts a flowchart of surgical steps 200 that can be taken to repair a heart valve leaflet according to an embodiment of the present invention. At step 202, the femoral or jugular vein is accessed via a cut down or Seldinger technique and an introducer with a hemostasis valve is inserted into the vein. In one embodiment, the outer diameter of the introducer is a maximum of 24 French. At step 202, access is gained to the right atrium 20 using a guide wire and an external guide catheter 102 is advanced over the guide wire to the ventricular apex. In one embodiment, the external guide catheter 102 is a side-exiting catheter. An internal guide catheter 104 is inserted into the external guide catheter following removal of the guide wire until it exits the external guide. At step 206, proper positioning of the internal guide catheter for puncture of the ventricular septal wall 12 is confirmed and a septal puncture device 106 is inserted into the internal guide 104 and advanced to the desired position at the septal wall 12 to puncture the septal wall 12. A guide wire can then be advanced through the internal guide 104 to maintain position in the left ventricle 14. The puncture tool 106 can be withdrawn and a dilator can be used to facilitate passage of the internal guide catheter 104 into the left ventricle 14 and then withdrawn.

At step 208, a suture deployment catheter 108 can be inserted into the internal guide catheter 104 and advanced in the left ventricle 14. The deployment catheter 108 can be positioned near the leaflet 16, capture the leaflet 16 with a moveable jaw 110, advance a suture needle 112 through the leaflet 16, withdraw the needle 112 back through the leaflet 16 and into the catheter 108, release the leaflet 16 and be withdrawn. In one embodiment, proper capture of the valve leaflet 16 is confirmed prior to advancing the needle 112 through the leaflet 16. In one embodiment, this can be done with a fiber optic visualization system. In one embodiment, deployment catheter 108 can be reinserted to deploy additional sutures 114 onto leaflet 16. In another embodiment, leaflet capture and suture deployment can be aided with an augmented reality navigation system utilizing magnetic tracking such as is disclosed in commonly owned, U.S. Provisional Application No. 61/565,795, which is hereby incorporated by reference. In some embodiments, deployment catheter 108 can deploy multiple sutures 114 onto leaflet 16 in a single insertion.

At step 210, the sutures 114 are threaded through a lumen 118 of a ventricular septal sealing device 117, which is then advanced to the ventricular septal wall 12 puncture site with a septal sealing catheter. The septal seal device 117 can have seal elements 116 deployed to seal the puncture and the septal sealing catheter is withdrawn, leaving the sutures 114 in the sealing device 117 and extending outward through the body. At step 212, the sutures 114 can be tensioned to a desired level for proper valve leaflet function. In one embodiment, proper tensioning of sutures 114 and valve leaflet function can be confirmed via transesophogeal echo. In one embodiment, tension of the sutures 114 can be released using a catheter 128 and readjusted.

At step 214, the sutures 114 are inserted into a lumen of an anchoring catheter 130, which is advanced through the internal guide 104 to the septal sealing device 117. An anchoring element 132 can then be deployed into the sealing device 117 to fix the sutures 114 in position in the sealing device 117 and the anchoring catheter 130 can be withdrawn. At step 216, a suture cutting catheter 136 is inserted into the guide catheter and used to cut the sutures adjacent the septal sealing device 117 with a cutting element 138. The cutting catheter 136, guide catheters 102, 104 and introducers can then all be withdrawn and the access site can be closed to complete the procedure.

Although the system and method described herein are primarily described in connection with intravenous access for a ventricular septal approach, it should be understood that the devices and methods described can be adapted for use with various other approaches. For example, the system can also provide venous access to the atrial septal wall for a trans-septal puncture that provides access to the left atrium. In addition, the system can be used to provide venous access to the left ventricle through the aortic valve.

It should further be noted that although the system and method described herein are primarily described with reference to repairing a heart valve leaflet, other tissue structures can be targeted for repair as well. For example, the papillary muscle, heart wall or any other intra-cardiac structure can be targeted for repair or anchoring.

In various embodiments, a heart valve repair system as described herein can be provided as a kit including the various catheters and devices described herein and instructions for repairing a heart valve of a patient as described herein. In one embodiment, the present application comprises the instructions. In another embodiment, an FDA required Instructions for Use can comprise the instructions.

Various embodiments of systems, devices, and methods have been described herein. These embodiments are given only by way of example and are not intended to limit the scope of the present invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

The invention claimed is:

1. A method of repairing a mitral valve in a beating heart of a patient, comprising:
   inserting an external guide catheter through a vein of a patient and into a right atrium of a heart of a patient;
   advancing the external guide catheter into a right ventricle of the patient's heart;
   advancing an internal guide catheter through the external guide catheter and advancing the internal guide catheter into the right ventricle;

puncturing an interventricular septum in the patient's heart to create an opening between the right ventricle and the left ventricle;

advancing the internal guide catheter through the opening in the interventricular septum and into the left ventricle;

advancing a deployment catheter through the internal guide catheter and advancing the deployment catheter through the interventricular septum and into the left ventricle;

deploying a suture onto a mitral valve leaflet with the deployment catheter;

advancing a sealing device through the internal guide catheter to the interventricular septum; and positioning the sealing device within the opening in the interventricular septum with the suture extending between the mitral valve leaflet that the suture is deployed onto and the sealing device.

2. The method of claim 1, wherein the step of positioning the sealing device within the opening in the interventricular septum is done after the step of deploying a suture onto the mitral valve.

3. The method of claim 1, wherein the step of deploying a suture onto the mitral valve with the deployment catheter includes:

capturing a mitral valve leaflet with a clamping mechanism of the deployment catheter; and inserting the suture through the mitral valve leaflet with a needle of the deployment catheter.

4. The method of claim 1, further comprising:

positioning the sealing device within the opening in the interventricular septum such that a proximal end of the suture extends from the mitral valve through the interventricular septum.

5. The method of claim 4, further comprising:

advancing a cutting catheter having a cutting tool through the internal guide catheter to the interventricular septum; and cutting the suture in the right ventricle adjacent the sealing device.

6. The method of claim 1, further comprising:

threading a proximal end of the suture through an anchoring device;

advancing the anchoring device through the internal guide catheter to the opening in the interventricular septum; and positioning the anchoring device with the sealing device within the interventricular septum such that the suture extends between the mitral valve and the opening in the interventricular septum.

7. A method of repairing a mitral valve in a beating heart of a patient comprising:

intravenously accessing a right ventricle of a beating heart of a patient;

creating an opening though an interventricular septum of the patient's heart between the right ventricle and the left ventricle;

positioning a deployment catheter containing a repair device in the left ventricle by extending the deployment catheter through the opening in the interventricular septum;

deploying a suture onto a mitral valve by drawing the suture through a mitral valve leaflet with a needle;

withdrawing the deployment catheter from the left ventricle through the interventricular septum.

8. The method of claim 7, further comprising:

positioning a sealing device within the opening in the interventricular septum; and connecting a locking device with the sealing device.

9. The method of claim 7, further comprising:

positioning a sealing device within the opening in the interventricular septum such that the suture extends from the mitral valve in the left ventricle through the interventricular septum and into the right ventricle.

10. The method of claim 9, further comprising:

advancing an anchoring device to the interventricular septum; and locking a position of the suture with respect to the sealing device with the anchoring device.

11. The method of claim 10, further comprising:

advancing a cutting tool to the interventricular septum; and cutting the suture in the right ventricle adjacent the sealing device.

12. A method, comprising:

providing a mitral valve repair system, the system including a side exiting external guide catheter, an internal guide catheter, a septal puncture tool and a deployment catheter;

providing instructions for deploying a suture onto a mitral valve of a beating heart of a patient with the mitral valve repair system, the instructions comprising:

inserting the side exiting external guide catheter through a vein of the patient and into a right atrium of the heart of the patient;

advancing the external guide catheter into the right ventricle of the patient's heart;

advancing the internal guide catheter through the external guide catheter and advancing the internal guide catheter into the right ventricle;

directing the septal puncture tool adjacent and generally transversely to the ventricular wall via the side exiting external guide catheter;

puncturing an interventricular septum in the patient's heart with the septal puncture tool to create an opening between the right ventricle and the left ventricle;

advancing the internal guide catheter through the opening in the interventricular septum into the left ventricle;

advancing the deployment catheter through the internal guide catheter and advancing the deployment catheter through the interventricular septum and into the left ventricle; and deploying a suture onto the mitral valve with the deployment catheter.

13. The method of claim 12, wherein the mitral valve repair system further includes a sealing device and the instructions further comprise:

advancing the sealing device through the internal guide catheter to the interventricular septum; and positioning the sealing device within the opening in the interventricular septum.

14. The method of claim 12, wherein the step of deploying a suture onto the mitral valve with the deployment catheter includes:

capturing a mitral valve leaflet with a clamping mechanism of the deployment catheter; and inserting the suture through the mitral valve leaflet with a needle of the deployment catheter.

15. The method of claim 12, wherein the mitral valve repair system further includes a sealing device and the instructions further comprise:

advancing the sealing device through the internal guide catheter to the interventricular septum; and positioning the sealing device within the opening in the interventricular septum such that a proximal end of the suture extends from the mitral valve through the interventricular septum.

16. The method of claim 15, wherein the mitral valve repair system further comprises a cutting catheter having a cutting tool and the instructions further comprise:

advancing the cutting catheter and cutting tool through the internal guide catheter to the interventricular septum; and cutting the suture in the right ventricle adjacent the sealing device.

17. The method of claim 12, wherein the mitral valve repair system further includes an anchoring device and the instructions further comprise:

threading a proximal end of the suture through the anchoring device;

advancing the anchoring device through the internal guide catheter to the opening in the interventricular septum; and positioning the anchoring device within the interventricular septum such that the suture extends between the mitral valve and the opening in the interventricular septum.

\* \* \* \* \*